US005904716A

United States Patent [19]
Gendler

[11] Patent Number: 5,904,716
[45] Date of Patent: *May 18, 1999

[54] METHOD FOR RECONSTITUTING CARTILAGE TISSUE USING DEMINERALIZED BONE AND PRODUCT THEREOF

[76] Inventor: El Gendler, 415 Georgina Ave., Santa Monica, Calif. 90402

[*] Notice: This patent issued on a continued prosecution application filed under 37 CFR 1.53(d), and is subject to the twenty year patent term provisions of 35 U.S.C. 154(a)(2).

[21] Appl. No.: 08/429,122

[22] Filed: Apr. 26, 1995

[51] Int. Cl.⁶ .......................................................... A61F 2/02
[52] U.S. Cl. ............................... 623/11; 623/20; 623/901; 623/66; 435/372; 435/366
[58] Field of Search .................................... 623/11, 16–20, 623/66, 901; 424/422, 423; 435/240.23, 372, 366

[56] References Cited

U.S. PATENT DOCUMENTS

| | | | |
|---|---|---|---|
| 4,299,819 | 11/1981 | Eisinger | 424/95 |
| 4,418,691 | 12/1983 | Yannag et al. | 128/156 |
| 4,458,678 | 7/1984 | Yannas et al. | 128/155 |
| 4,505,266 | 3/1985 | Yannas et al. | 128/1 |
| 4,553,272 | 11/1985 | Mears | 623/1 |
| 4,627,853 | 12/1986 | Campbell et al. | 623/16 |
| 4,681,763 | 7/1987 | Nathanson et al. | 424/95 |
| 4,804,382 | 2/1989 | Turina et al. | 623/1 |

(List continued on next page.)

FOREIGN PATENT DOCUMENTS

| | | |
|---|---|---|
| 0 046 039 | 2/1982 | European Pat. Off. . |
| 0 128 733 | 12/1984 | European Pat. Off. . |
| 0 131 868 | 1/1985 | European Pat. Off. . |
| 0 136 490 | 4/1985 | European Pat. Off. . |
| 0 147 178 | 7/1985 | European Pat. Off. . |
| 0 150 572 | 8/1985 | European Pat. Off. . |
| 0 177 915 | 4/1986 | European Pat. Off. . |
| 0 267 015 | 5/1988 | European Pat. Off. . |
| 2 092 155 | 8/1982 | United Kingdom . |
| 2 162 851 | 2/1986 | United Kingdom . |
| 2 172 890 | 10/1986 | United Kingdom . |
| WO83/04030 | 11/1983 | WIPO . |
| WO85/00369 | 1/1985 | WIPO . |
| WO85/01284 | 3/1985 | WIPO . |
| WO86/02271 | 4/1986 | WIPO . |

OTHER PUBLICATIONS

Bettex–Galand et al., Experientia, 43 (6), 610–611 (1987).
Macklis et al., "Cross–Linked Collagen Surface for Cell Culture That is Stable, Uniform, and . . .", *In Vitro Cellular & Developmental Biology*, 21, 189–194, 1985.
Watt et al., "Prolonged Expression of Differentiated Phenotype by Chondrocytes Cultured at Low Density . . .", *Differentiation*, 38, 140–147, 1988.
Delbruck et al., "In–Vitro Culture of Human Chondrocytes From Adult Subjects", *Connective Tissue Research*, 15, 155–172, 1986.
Cheung, "In Vitro Cartilage Formation on Porous Hydroxyapatite Ceramic Granules", *In Vitro Cellular & Developmental Biology*, 21, 353–357, 1985.
Upton, "Neocartilage Derived from Transplanted Perichondrium: What is it?", *Plastic and Reconstructive Surgery*, 68(2), 166–174, (Aug. 1981).
Wozney et al., "Novel Regulators of Bone Formation: Molecular Clones and Activities", *Science*, 242, 1528–1534, (Dec. 16, 1988).
Streuli et al., "Expression of Extracellular Matrix Components Is Regulated by Substratum", *Journal of Cell Biology*, 110, 1405–1415 (Apr. 1990).
Buck, "Cell Surface Receptors For Extracellular Matrix Molecules", *Ann. Rv. Cell Biol.*, 3, 179–205 (1987).

*Primary Examiner*—Robert A. Clarke
*Attorney, Agent, or Firm*—Leydig, Voit & Mayer, Ltd.

[57] ABSTRACT

Continuous, flexible demineralized bone is used as a support for growing cartilage tissue that may be used for implantation into a patient to replace defective of missing cartilage.

11 Claims, 2 Drawing Sheets

U.S. PATENT DOCUMENTS

| | | | |
|---|---|---|---|
| 4,883,487 | 11/1989 | Yoshizato et al. | 623/15 |
| 4,904,259 | 2/1990 | Itay | 623/16 |
| 4,932,973 | 6/1990 | Gendler | 623/16 |
| 4,960,423 | 10/1990 | Smith | 623/1 |
| 5,015,584 | 5/1991 | Bryak | 435/240 |
| 5,035,708 | 7/1991 | Alchas et al. | 623/1 |
| 5,041,138 | 8/1991 | Vacanti et al. | 623/16 |
| 5,131,907 | 7/1992 | Williams et al. | 600/36 |
| 5,236,456 | 8/1993 | O'Leary et al. | |
| 5,306,304 | 4/1994 | Gendler | 623/16 |
| 5,326,357 | 7/1994 | Kandel | 623/16 |
| 5,376,118 | 12/1994 | Kaplan et al. | 623/11 |

METHOD FOR RECONSTITUTING CARTILAGE TISSUE USING DEMINERALIZED BONE AND PRODUCT THEREOF

FIELD OF THE INVENTION

The present invention relates to reconstituted cartilage tissue; to a method for producing reconstituted cartilage tissue by use of a biocompatible support material as a substrate for impregnation with living cells to enable cell growth and division; and to cartilage tissue reconstituted in vitro from isolated chondrocytes.

BACKGROUND OF THE INVENTION

This invention is primarily directed to reconstituted articular cartilage, which is a specialized tissue found at the end of articulating bones. Cartilage, unlike other connective tissues, lacks blood vessels, nerves lymphatics and basement membrane. It is responsible for the distribution of load resistance to compressive forces, and the smooth gliding that is part of joint function.

Cartilage is composed of chondrocytes which synthesize an abundant extracellular matrix, which is composed of water, collagens, proteoglycans and noncollagenous proteins and lipids. Collagen serves to trap proteoglycans and to provide tensile strength to the tissue.

Damage of cartilage produced by disease, such as arthritis, or trauma is a major cause of physical deformity and debilitation. In medicine today, the primary therapy for loss of cartilage is replacement with a prosthetic material, such as silicone for cosmetic repairs, or metal alloys for joint relinement. Placement of prostheses is commonly associated with significant loss of underlying tissue and bone without recovery of the full function allowed by the original cartilage, as well as the irritating presence of a foreign body. Other long term problems associated with a permanent foreign body can include infection, erosion and instability Very little has ever been actually used to replace the cartilage overlaying bone surfaces. To date, the growth of new cartilage from either transplantation of autologous or allogeneic cartilage has been largely unsuccessful. Microscopic islands of cartilage formation have recently been demonstrated histologically in vivo by implanting recombinant bone morphogenic protein, as reported by J. M. Wozney, et al., Science, 242, 1528–1534, (Dec. 16, 1988). Limited success has been achieved in making neocartilage using free autogenous grafts of perichondrial flaps, as described by J. Upton, Plastic and Reconstructive Surgery, 68(2), 166–174; (August 1981).

It is also known in the art to use cells harvested from an organism for implantation into the same or a different organism. Such techniques are shown is U.S. Pat. Nos. 4,299,819, 4,418,691, 4,458,678, 4,505,266, 4,553,272, 4,804,382, 4,883,487, 4,904,259, 4,960,423, 5,015,584, 5,035,708, and 5,041,138 the disclosures of which are expressly incorporated herein by reference. In these references, the cells are seeded on a biocompatible support material and implanted into a desired site for tissue repair, with or without a step of cell cultivation in vitro, depending upon the type of tissue being replaced and the extent of tissue damage at the site needing repair. The limitations of his technique are associated with the substrate material. Typically, bioabsorbable substrates are used for cell seeding. During cell cultivation in vitro, portions of these substrate materials are absorbed, leaving a support material for implantation which does not have the strength and resiliency to function as a prosthetic device at the site of tissue damage while additional tissue ingrowth and cell division takes place.

The provision of a suitable support material is a critical part of the in vitro cell cultivation technique. This is because most types of tissue will not grow or divide in suspension; a solid support is necessary for the cells to perform their normal functions. However, because the growing cells must receive nutrients from the nutrient media and eliminate cell waste products, all without a circulatory system which normally performs this function, the support upon which the cells are placed must allow for this exchange. Additionally, many cell cultures require a support coated with materials which form a part of the extracellular matrix, a collection of polysaccharides and proteins which exist outside the cell's membrane.

Cheung (in vitro Cell. Dev. Biol. 21:353, 1985) teaches a method of culturing canine chondrocytes on porous hydroxyapatite ceramic granules. The cells reportedly proliferated and secreted metachromatic extracellular matrix for up to 13 months. An agarose gel matrix has also been described as suitable for the in vitro culture of human chondrocytes (Delbruck et al., Conn. Tiss. Res. 15:155, 1986). Watt and Dudhia (Differentiation 38:140, 1988) disclose a composite gel of collagen and agarose for the culture of porcine chondrocytes. The composite gel prevented chondrocytes spreading. However, virtually no extracellular matrix was secreted in the low density culture composite gels.

Macklis et al. (in vitro Cell. Develop. Biol. 21:180, 1985) teach a collagen surface for culturing peripheral nervous system cells, comprising collagen derivatized to polystyrene plastic culture dishes. Macklis et al. disclose that the derivatized coating process yielded enhanced collagen adhesion and increased long term survival of cultured nerve cells, compared to collagen coating produced by absorption techniques.

U.S. Pat. No. 5,376,118, relates to the use of a support material fabricated from semiabsorbable, composite yarn as a support for cell growth in vitro. The support comprises a nonabsorbable, elastic core yarn and at least one absorbable, relatively inelastic sheath yarn imparting transverse strength to the composite yarn. The cells that can be grown on the support allegedly encompass endothelial cells, epidermal cells, muscle cells, bone cells, and cartilage cells.

U.S. Pat. No. 5,326,357, relates to the use of a substrate for chondrocyte cell growth in vitro. The substrate that is employed is a synthetic substrate, Millicell®-CM, coated with attachment factors.

U.S. Pat. No. 5,041,138, relates to a method for making a cartilaginous structure by use of a biocompatible, biodegradable synthetic polymeric matrix for chondrocyte cell growth in vitro, and its use for replacing defective or missing cartilage.

To date, none of the aforementioned methods of cartilage growth and replacement have found wide acceptance. As can be seen from the descriptions, the methods that use chondrocyte cell growth in vitro, rely upon synthetic support media that are foreign to the body, resulting in problems associated with the introduction of foreign compositions into the body.

A need therefore exist for a method for growing chondrocytes ex vivo by use of a supportive substrate that will find universal acceptance upon implantation for reconstructive use, while providing the characteristics necessary for cell growth in vitro.

SUMMARY OF THE INVENTION

The present invention provides a method for growing chondrocytes ex vivo, by use of a supportive substrate that is uniquely biocompatible, making the resulting structure with cartilage growth thereon especially useful for implantation for reconstructive use, while the structure provides the characteristics necessary for cell growth in vitro.

In accordance with the present invention, the supportive substrate that is used for chondrocyte growth in vitro is a continuous, flexible sheet of demineralized natural bone, having a thickness less than about 1.5 mm. As used herein below, all reference to use of a substrate is meant to refer to the aforementioned flexible sheet of demineralized bone.

Use of such a substrate provides a surface with physiological orientation of collagen fibers and physiological micro-anatomy and micro-porosity. This provides chondrocytes with a physiological receptor surface for attachment and allows for good exchange of nutrients and gases approximately equivalent to that which occurs in vivo.

The surface of the substrate, which is pliable and flexible, easily adopts to the surface of exposed subchondral bone, which can be microperforated to stimulate outward migration of undifferentiated mesenchymal cells of bone marrow. Because the substrate is a membrane made from demineralized bone it is capable to act as osteoinductive agent. Thus, undifferentiated mesenchymal cells coming in contact with the substrate differentiates into cartilage and bone producing cells. Eventually the substrate, after implantation become replaced by new live bone, which unites with exposed subchondral bone and provides a physiological support for in vitro grown chondrocytes. Total replacement of the substrate in normal conditions occurs within six months after implantation.

Thus an advantage of the use of the present substrate over synthetic membranes is the physiological orientation of the resulting collagen fibers, and physiological micro-anatomy of the bone itself that is present in the substrate. This provides physiological receptor surface for attachment and proliferation of chondrocytes in vitro. Physiological micro-porosity of human bone thus provides optimal exchange of nutrients and gases.

After the implantation, the substrate demonstrates osteoinductive phenomena and instead of being resorbed by ingrowing blood vessels, becomes replaced by new live bone within six-month period. Replacement of the substrate with new live bone provides chondrocytes with physiological attachment base through which physiological exchange of nutrients and gases occurs.

Thus, the present invention also relates to a method for producing reconstituted cartilage tissue comprising removing cartilage tissue, particularly articular cartilage from the joint of an animal; digesting said cartilage tissue to obtain isolated chondrocytes; forming a monolayer of chondrocytes on a substrate; culturing the chondrocytes in growth media to produce a tissue having a biochemical composition and physiological organization substantially the same as articular cartilage tissue.

The invention further relates to artificial cartilage tissue reconstituted in vitro by digesting cartilage tissue to obtain isolated chondrocytes; forming a monolayer of chondrocytes on a substrate; culturing the chondrocytes and growth medium to produce a tissue having a biochemical composition and physiological organization substantially the same as normal mammalian cartilage tissue.

The invention still further relates to a method of using the reconstituted cartilage tissue structure of the present invention to test pharmaceutical preparations for efficacy in the treatment of diseases of the joint and to a method of using the reconstituted tissue structure of the present invention as an implant to replace or repair damaged or deficient cartilage.

DETAILED DESCRIPTION OF THE PREFERRED EMBODIMENTS

Figure 1:
FIG. 1 shows chondrocytes that have grown in vitro as multi-layer structure closely adhering to the surface of the substrate.
Figure 2:
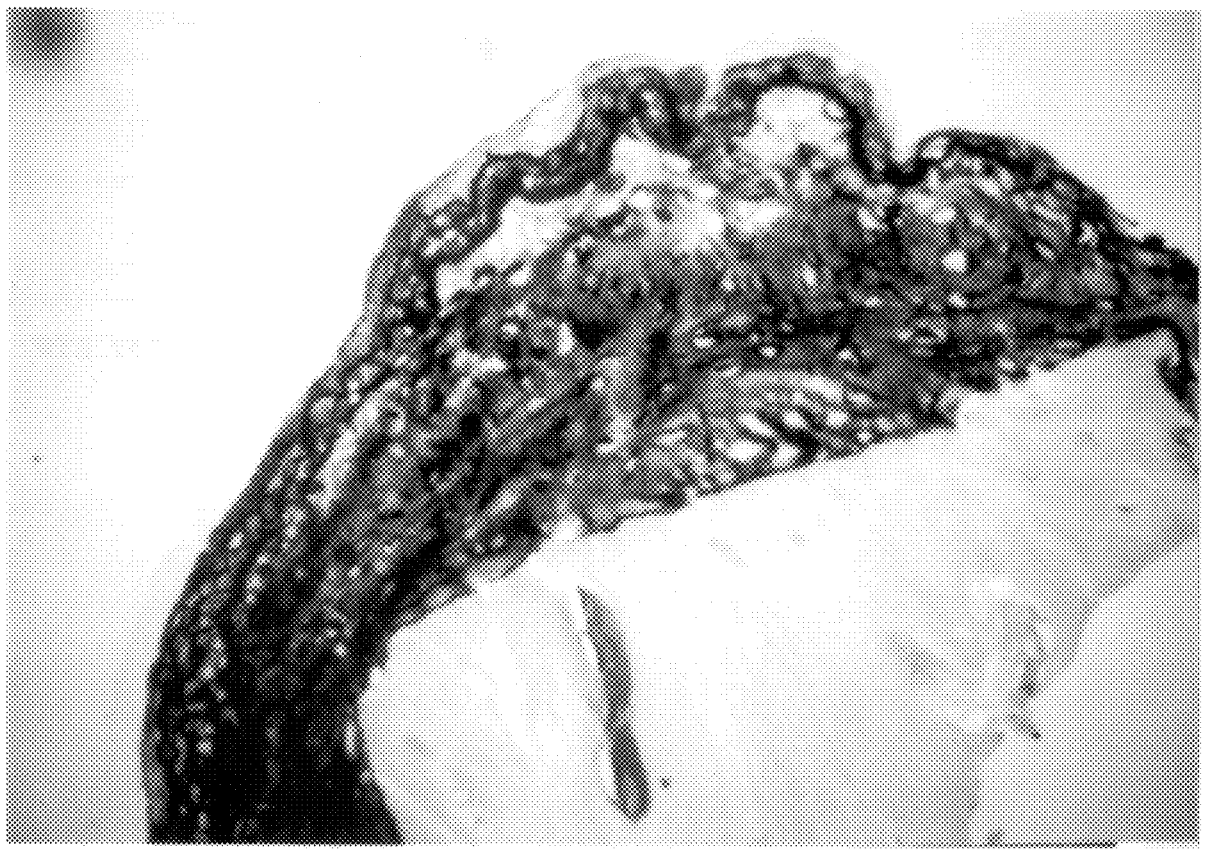
FIG. 2 shows chondrocyte growth that follows the contour of the substrate even in perpendicular directions. Growth of chondrocytes extends into Haversian channels which constitute a natural porosity of the substrate. This results in very tenacious attachment between new cartilage and the substrate.

As indicated above the substrate used in accordance with the present invention comprises a continuous, flexible sheet of demineralized natural bone, having a thickness less than about 1.5 mm. Such a structure is taught and can be obtained in accordance with U.S. Pat. No. 5,306,304.

There are several kinds of cartilage. Hyaline cartilage is a bluish-white, glassy translucent cartilage having a homogeneous matrix containing collagenous fibers which is found in articular cartilage, in costal cartilages, in septum of the nose, in larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is primarily found in the epiglottis, the external ear, and the auditory tube. As described below, cartilage implants can be formed of one or more types of cartilage, depending primarily on the location of the implant and the type of cartilage cells seeded onto the substrate.

In one embodiment the substrate is placed in culture media containing chondrocytes, where the chondrocytes attach to the fibers in multiple layers. Usually, the chondrocytes retain their normal rounded configuration, which appears to be useful for the chondrocytes to maintain their normal function and secrete a cartilage matrix and other bioactive molecules such as angiogenesis inhibiting factor.

The composite structure of substrate and cells can be transplanted into animals without disrupting the complex of attached chondrocytes. Transplantation of this composite containing a high density of normally functioning chondrocytes with a large surface area into an animal allows the cells to obtain adequate nutrition by diffusion and successful engraftment of functioning chondrocytes with cartilage formation even in the initial absence of vascularization.

Chondrocytes are initially isolated and cultured using techniques known to those skilled in the art of tissue culture. In contrast to some types of cells, chondrocytes can be seeded directly onto the substrate and implanted without first proliferating the cells in vitro. If insufficient cell numbers are available for implantation, cells are first cultured in vitro on the matrix. Once the cells have begun to grow and cover the matrix, they can be implanted in a patient at a site appropriate for attachment, growth and function.

Because the substrate will eventually be resorbed, angiogenic and other bioactive compounds can be incorporated directly into the substrate so that they are slowly released as the substrate degrades in vivo. As the cell-substrate composite is vascularized and the structure degrades, the cells will differentiate according to their inherent characteristics.

The reconstituted cartilage tissue of the present invention may be prepared from chondrocytes isolated from articular cartilage from animals, preferably humans. A particularly useful system may be prepared from chondrocytes isolated from human articular cartilage, for example from the kace joint. The chondrocytes may be isolated by sequential enzyme digestion techniques, such as those described in Kandel et al., Biochem. Biophys. Acta. 1035:130, 1990. For example, the cartilage may be treated with 0.5% protease followed by 0.04% bacterial collagenase.

The living cells contact an exterior portion of the substrate. Usually, the cells will be cultured in vitro on the substrate. The support material and living cells may then placed in contact with living tissue to function as a tissue repair device.

The chondrocytes seeded on the coated substrate, may be grown in suitable culture conditions. Broadly, in vitro cell cultivation involves harvesting the desired cells from the host organism, placing them on the substrate, and providing an appropriate nutrient medium and temperature and atmospheric conditions to allow the cells to grow and divide. In general, the nutrient medium contains amino acids, vitamins, salts, glucose and antibiotics. The support material impregnated with cells is placed in a suitable container in communication with the appropriate nutrient medium and maintained in an incubator until the desired number of cell divisions have occurred.

Examples of suitable culture media are known in the art, such as Ham's F12 medium. The culture medium may contain serum, for example fetal bovine serum in a concentration range of about 2–15% and may further contain growth factors and ascorbic acid. The cells may be cultured at 37° C. in a humidified atmosphere supplemented with $CO_2$, for at least 2 weeks.

The cells, after harvest from an organism, either as an intact tissue structure or as a suspension formed, e.g., by centrifugation or ultrasonic tissue disruption, are placed in contact with a support material. Exemplary techniques for forming cell suspensions are described in U.S. Pat. Nos. 4,418,691, 4,458,678, 4,505,266, and 5,041,138.

Following formation of a suspension, the support material must be impregnated with the cells such that the cells are located on the surfaces of the various individual fibers. This impregnation may be accomplished in a variety of ways depending upon the shape and thickness of the support material. For example, the support material of the present invention may be impregnated by immersion in a cell suspension, spraying with a cell suspension, injection with a cell suspension via hypodermic needle, centrifugation of the support material with a cell suspension or any other technique in the art for impregnating a material with a suspension. Usually, the impregnation step accomplished so that the cells are placed not merely on the surface of an prosthetic implant, but are located throughout the material, adhering to the surface of the support material. The ability to situate cells on the substrate permits a higher density of cells within a given implant. As a result, faster rates of tissue formation throughout the device as well as enhanced tissue ingrowth rates and vascularization following implantation of a seeded device into the host organism are achieved.

It is within the scope of this invention to coat or impregnate the support material with, or otherwise apply thereto, one or more materials which enhance its functionality, e.g., surgically useful substances, such as those which accelerate or beneficially modify the healing process when the support material is applied to a graft site. Additionally, components of the extracellular matrix, e.g., polysaccharides and proteins such as collagen, can be coated onto the prosthetic support material of the invention to enhance cell growth and division.

As indicated, the reconstituted cartilage tissue of the present invention also can be used as a model system for in vitro studies of cartilage structure, function and development. In particular, the reconstituted cartilage of the present invention may be used in the testing of pharmaceutical preparations useful in the treatment of diseases of the joint, for example osteoarthritis, inflammatory arthropathies, septic arthritis and crystalline arthropathies.

The reconstituted cartilage tissue of the invention is principally used as an implant for use in the joints of patients to replace or repair damaged or deficient cartilage.

What is claimed is:

1. A biological material comprising cartilage tissue reconstituted on a substrate in vitro from isolated chondrocytes wherein the substrate is a continuous, flexible sheet of demineralized natural bone, having a thickness less than about 1.5 mm and chondrocyte growth extends into Haversian channels of the substrate.

2. A method for producing a biological material comprising reconstituted cartilage tissue, wherein the method comprises isolating chondrocytes from cartilage tissue, contacting a substrate comprised of a continuous, flexible sheet of demineralized natural bone, having a thickness less than about 1.5 mm, with said chondrocytes, and culturing the chondrocytes on the substrate in growth media to produce a biological material characterized by a continuous layer of cartilage tissue and chondrocyte growth extends into Haversian channels of the substrate.

3. The method of claim 2 wherein the chondrocytes are isolated from human articular cartilage tissue.

4. The method of claim 3, wherein the chondrocytes are isolated by sequential enzyme digestion techniques.

5. A method for making a cartilaginous structure comprising providing a substrate comprised of a continuous, flexible sheet of demineralized natural bone, having a thickness less than about 1.5 mm, in a nutrient environment and attaching cartilage cells to the substrate to form a cartilaginous structure which covers the surface of the substrate and chondrocyte growth extends into Haversian channels of the substrate, said substrate being suitable for implantation into a patient to replace defective or missing cartilage.

6. The method of claim 5 further comprising implanting the attached cells on the substrate in an animal without first proliferating the cells on the substrate in vitro.

7. The method of claim 5 further comprising proliferating the cells on the substrate in vitro in a nutrient media, then implanting a structure comprising the expanded cells on the substrate in vitro.

8. The method of claim 7 wherein the structure is implanted to repair cartilage damaged by inflammation.

9. The method of claim 7 wherein the structure is implanted to repair cartilage damaged by trauma.

10. The method of claim 7 wherein the structure is implanted to repair cartilage damaged by aging.

11. The method of claim 7 wherein the structure is implanted to repair cartilage which is congenitally defective.

* * * * *